US011028069B2

(12) United States Patent
Mitsuya

(10) Patent No.: US 11,028,069 B2
(45) Date of Patent: Jun. 8, 2021

(54) SALT OF SUBSTITUTED PIPERIDINE COMPOUND

(71) Applicant: TAIHO PHARMACEUTICAL CO., LTD., Chiyoda-ku (JP)

(72) Inventor: Morihiro Mitsuya, Tsukuba (JP)

(73) Assignee: TAIHO PHARMACEUTICAL CO., LTD., Chiyoda-ku (JP)

(*) Notice: Subject to any disclaimer, the term of this patent is extended or adjusted under 35 U.S.C. 154(b) by 0 days.

(21) Appl. No.: 16/472,000

(22) PCT Filed: Dec. 22, 2017

(86) PCT No.: PCT/JP2017/046249
§ 371 (c)(1),
(2) Date: Jun. 20, 2019

(87) PCT Pub. No.: WO2018/117267
PCT Pub. Date: Jun. 28, 2018

(65) Prior Publication Data
US 2020/0087282 A1 Mar. 19, 2020

(30) Foreign Application Priority Data
Dec. 22, 2016 (JP) .............................. JP2016-249767

(51) Int. Cl.
C07D 401/14 (2006.01)
A61K 9/00 (2006.01)
A61P 35/00 (2006.01)

(52) U.S. Cl.
CPC .......... C07D 401/14 (2013.01); A61K 9/0053 (2013.01)

(58) Field of Classification Search
CPC ................................ C07D 401/14; A61P 35/00
USPC ........................................... 546/194; 514/318
See application file for complete search history.

(56) References Cited

U.S. PATENT DOCUMENTS

| 6,627,646 B2 * | 9/2003 | Bakale ..................... A61P 37/08 514/322 |
| 9,012,475 B2 | 4/2015 | Hirai et al. |
| 2015/0045342 A1 | 2/2015 | Sugimoto et al. |
| 2015/0065479 A1 | 3/2015 | Hirai et al. |
| 2016/0228427 A1 | 8/2016 | Sugimoto et al. |

FOREIGN PATENT DOCUMENTS

WO    WO 2013/129443 A1    9/2013

OTHER PUBLICATIONS

Bernstein, "Polymorphism in . . . " p. 115-118, 272. (Year: 2002).*
Davidovich et al., "Detection of polymorphism . . . " Am. Pharm. Rev. 7(1) p. 10, 12, 14, 16, 100 . . . (Year: 2004).*
Dean "Analytical Chem . . . " p. 10.24-10.26. (Year: 1995).*
Ivanisevic et al. "Use of X-ray . . . " Pharm. Sci. Encycl. p. 1-42 . . . (Year: 2010).*
Seddon "Pseudopolymoroh . . . " Crystal Growth & desiqn v.4(6) p. 1087 (2 pages from internet). (Year: 2004).*
Rodriguez-Spong et al., "General principles, etc.," Adv. Drug Delivery Reviews 56 241-274. (Year: 2004).*
Kirk-Othmer Encyclopedia of Chemical Technology, 8, pp. 95-147. (Year: 2002).*
Vippagunta et al., "Crystalline Solids", Advanced Drug Delivery Reviews 48 .3-26. (Year: 2001).*
Guillory (in Brittain ed.), "Polymorphism in Pharmaceutical Solids.," NY: Marcel Dekker, Inc., 1-2, 183-226. (Year: 1999).*
Braga et al., "Making crystals from . . . " J. Royal Soc. Chem. Commun. p. 3635-3645. (Year: 2005).*
CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffaretal., "Polymorphism and Drug Availability, etc.," J of Pharm. (Lahore), 1(1), 59-66. (Year: 1979).*
U.S. Pharmacopia #23, National Formulary #18,1843-1844. (Year: 1995).*
Doelker, english translation of S.T.P. Pratiques, 9(5), 399-409, pp. 1-33. (Year: 1999).*
Doelker, english translation of Ann. Pharm. Fr.,60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull., 47(6) 852-8569. (Year: 1999).*
International Search Report dated Feb. 20, 2018 in PCT/JP2017/046249, 3pages.

(Continued)

Primary Examiner — Patricia L Morris
(74) Attorney, Agent, or Firm — Oblon, McClelland, Maier & Neustadt, L.L.P.

(57) ABSTRACT

An object of the present invention is to provide a salt of the compound 1-(2,3-dichlorobenzoyl)-4-((5-fluoro-6-(5-methyl-1H-pyrazol-3-ylamino)pyridin-2-yl)methyl)piperidine-4-carboxylic acid, useful as an antitumor agent, and crystals thereof which are excellent in solubility, stability, and oral absorption and can be produced in large quantities. The present invention relates to a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid and crystals of the hydrochloride salt having characteristic peaks at particular diffraction angles in powder X-ray diffraction spectrum.

9 Claims, 12 Drawing Sheets

(56) References Cited

OTHER PUBLICATIONS

Noriyuki Takata et al., "API Form Screening and Selection in Drug Discovery Stage", Pharm Stage, vol. 6., No. 10, Jan. 15, 2007, 9 pages (with English translation).
Noriaki Hirayama, "Organic Compound Crystal Production Handbook-Principles and Knowhow", Maruzen, Jul. 25, 2008, 31 pages (with English translation).
Extended European Search Report dated Apr. 17, 2020 in European Patent Application No. 17882687.1, 10 pages.
Caira, M.R., "Crystalline Polymorphism of Organic Compounds", Topics in Current Chemistry, vol. 198, Jan. 1, 1998, XP001156954, pp. 163-208.

* cited by examiner

SALT OF SUBSTITUTED PIPERIDINE COMPOUND

TECHNICAL FIELD

The present invention relates to a substituted piperidine compound excellent in solubility and oral absorption and useful as an antitumor agent and particularly to a hydrochloride salt thereof that is a crystal. The present invention also relates to a pharmaceutical composition comprising the hydrochloride salt of the substituted piperidine compound and particularly to a pharmaceutical composition for oral administration. The present invention further relates to a method for producing the hydrochloride salt of the substituted piperidine compound, or crystals thereof.

BACKGROUND ART

Pharmaceutical compositions for oral administration usually require excellent solubility, stability, and oral absorption of their active ingredients, methods that allow production in large quantities, and the like. When active ingredients are organic compounds, salts of the active ingredients are studied for the improvement of solubility and the like, but it is difficult to predict optimal salts.

Moreover, in the case where crystal polymorphs of a compound (crystals of the same molecule in which the arrangement of atoms or molecules is different) exist, they have different peaks obtained by a powder X-ray diffraction measurement (XRD measurement). Crystal polymorphs are known to be different in solubility, stability, oral absorption, and the like, and it is desired in the development of pharmaceutical preparations to find an optimal crystal form from various viewpoints.

A plurality of Aurora A inhibitors have been reported as antitumor agents so far. As a compound that has excellent Aurora A inhibiting effect and exhibits the anti-tumor activity, 1-(2,3-dichlorobenzoyl)-4-((5-fluoro-6-(5-methyl-1H-pyrazol-3-ylamino)pyridin-2-yl)methyl)piperidine-4-carboxylic acid (hereinafter, also referred to as "Compound 1") has been reported (Patent Literatures 1, 2).

CITATION LIST

Patent Literature

Patent Literature 1: International Publication No. WO 2013/129443
Patent Literature 2: U.S. Pat. No. 9,012,475

SUMMARY OF INVENTION

Technical Problem

However, these reports include no detailed studies on salts of 1-(2,3-dichlorobenzoyl)-4-((5-fluoro-6-(5-methyl-1H-pyrazol-3-ylamino)pyridin-2-yl)methyl)piperidine-4-carboxylic acid (Compound 1) and crystals of the salts, or no description about solubility, stability, and oral absorption.

Meanwhile, the free form of Compound 1 forming no salt was found to have low solubility and oral absorption. Among administration forms of agents, oral administration is a mode of administration with a few burdens for patients and, therefore, the improvement of oral absorption is a very important issue for the formulation of Compound 1.

Accordingly, an object of the present invention is to provide a salt of Compound 1 and a crystal thereof, that are useful as an antitumor agent and excellent in solubility, stability, and oral absorption and can be produced in large quantities.

Solution to Problem

The present inventor has studied properties of various salts of Compound 1 and repeated diligent investigations and, as a result, found that the hydrochloride salt thereof is particularly excellent in solubility and oral absorption, and that crystals thereof are excellent in solubility, stability, and oral absorption and can be produced in large quantities, thereby completing the present invention.

Accordingly, the present invention relates to the following [1] to [25].

[1] A hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid.

[2] The salt according to [1] described above, wherein the salt is a crystal having characteristic peaks at at least 3 or more diffraction angles (2θ±0.2°) selected from 12.83°, 13.54°, 16.20°, 18.27°, 23.80° 29.10° and 32.83° in powder X-ray diffraction spectrum.

[3] The salt according to [1] or [2] described above, wherein the salt is a crystal having characteristic peaks at diffraction angles (2θ±0.2°) of 12.83°, 13.54°, 16.20° 18.27° 23.80°, 29.10°, and 32.83° in powder X-ray diffraction spectrum.

[4] The salt according to any of [1] to [3] described above, wherein the salt is characterized by a powder X-ray diffraction spectrum depicted in FIG. 1.

[5] The salt according to any of [1] to [4] described above, wherein the salt has an endothermic peak at 234±5° C. in differential thermal analysis.

[6] The salt according to any of [1] to [5] described above, wherein a weight ratio is 90% or more.

[7] A hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid, produced by a method characterized by use of a solvent comprising one or two or more selected from the group of water, a $C_{1-6}$ alcohol, a $C_{1-6}$ ester, a $C_{1-6}$ ketone, a $C_{1-6}$ ether, a $C_{1-6}$ hydrocarbon, an aprotic polar solvent, and an aqueous hydrogen halide solution.

[8] The hydrochloride salt according to [7], wherein the hydrochloride salt is produced by a method characterized by use of one or two or more solvents selected from the group of a $C_{1-6}$ alcohol, a $C_{1-6}$ ester, a $C_{1-6}$ ketone and an aqueous hydrogen halide solution.

[9] The hydrochloride salt according to [7] or [8], wherein the hydrochloride salt is produced by a method characterized by use of one or two or more solvents selected from the group of ethyl acetate, ethanol, and hydrochloric acid.

[10] The hydrochloride salt according to any one of [7] to [9], wherein the hydrochloride salt is produced by a method characterized by use of a mixed solvent of ethyl acetate, ethanol, and hydrochloric acid.

[11] The hydrochloride salt according to any of [7] to [10] described above, wherein the hydrochloride salt comprises a crystal having characteristic peaks at at least 3 or more diffraction angles (2θ±0.2°) selected from 12.83°, 13.54°, 16.20°, 18.27°, 23.80°, 29.10°, and 32.83° in powder X-ray diffraction spectrum.

[12] The hydrochloride salt according to any of [7] to [11] described above, wherein the hydrochloride salt comprises a crystal having characteristic peaks at diffraction angles (2θ±0.2°) of 12.83°, 13.54°, 16.20°, 18.27°, 23.80°, 29.10° and 32.83° in powder X-ray diffraction spectrum.

[13] The hydrochloride salt according to any of [7] to [12] described above, wherein the hydrochloride salt is characterized by a powder X-ray diffraction spectrum depicted in FIG. 1.

[14] The hydrochloride salt according to any of [7] to [13] described above, wherein the hydrochloride salt has an endothermic peak at 234±5° C. in differential thermal analysis.

[15] A hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid, produced by a method of production, comprising:

step (1): a step of adding 1-(2,3-dichlorobenzoyl)-4-((5-fluoro-6-(5-methyl-1H-pyrazol-3-ylamino)pyridin-2-yl)methyl)piperidine-4-carboxylic acid and hydrochloric acid to a solvent; and step (2): a step of stirring the solvent obtained in the step (1) to precipitate a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid.

[16] The salt according to [15] described above, wherein the salt comprises a crystal having characteristic peaks at at least 3 or more diffraction angles (2θ±0.2°) selected from 12.83°, 13.54°, 16.20°, 18.27°, 23.80°, 29.10°, and 32.83° in powder X-ray diffraction spectrum.

[17] The salt according to [15] or [16] described above, wherein the salt comprises a crystal having characteristic peaks at diffraction angles (2θ±0.2°) of 12.83°, 13.54°, 16.20°, 18.27°, 23.80° 29.10° and 32.83° in powder X-ray diffraction spectrum.

[18] The salt according to any of [15] to [17] described above, wherein the salt is characterized by a powder X-ray diffraction spectrum depicted in FIG. 1.

[19] The salt according to any of [15] to [18] described above, wherein the solvent in the step (1) is selected from a $C_{1-6}$ alcohol, a $C_{1-6}$ ester, a $C_{1-6}$ ketone, or a mixed solvent thereof.

[20] The salt according to any of [15] to [19] described above, wherein the solvent in the step (1) is selected from ethanol, ethyl acetate, acetone, or a mixed solvent thereof.

[21] A pharmaceutical composition comprising a salt according to any of [1] to [20] described above, or a crystal thereof.

[22] A pharmaceutical composition for oral administration, comprising a salt according to any of [1] to [20] described above, or a crystal thereof.

[23] A method for producing a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid, characterized by use of a solvent comprising one or two or more selected from the group of water, a $C_{1-6}$ alcohol, a $C_{1-6}$ ester, a $C_{1-6}$ ketone, a $C_{1-6}$ ether, a $C_{1-6}$ hydrocarbon, an aprotic polar solvent, and an aqueous hydrogen halide solution.

[24] A method for producing a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid, or a crystal thereof comprising:

step (1): a step of adding 1-(2,3-dichlorobenzoyl)-4-((5-fluoro-6-(5-methyl-1H-pyrazol-3-ylamino)pyridin-2-yl)methyl)piperidine-4-carboxylic acid and hydrochloric acid to a solvent; and step (2): a step of stirring the solvent obtained in the step (1) to precipitate a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid.

[25] The method according to [24] described above, wherein the solvent in the step (1) is selected from a $C_{1-6}$ alcohol, a $C_{1-6}$ ester, a $C_{1-6}$ ketone, or a mixed solvent thereof.

The description of the present application encompasses the contents disclosed in JP Patent Application No. 2016-249767, which the priority of the present application is based on.

Advantageous Effects of Invention

According to the present invention, the hydrochloride salt of Compound 1 is excellent in solubility and oral absorption and shows promise in use in pharmaceutical preparations, particularly pharmaceutical preparations for oral administration, since it can be obtained as crystals that are excellent in solubility, stability, and oral absorption and can be produced in large quantities.

DESCRIPTION OF EMBODIMENTS

Figure 1:
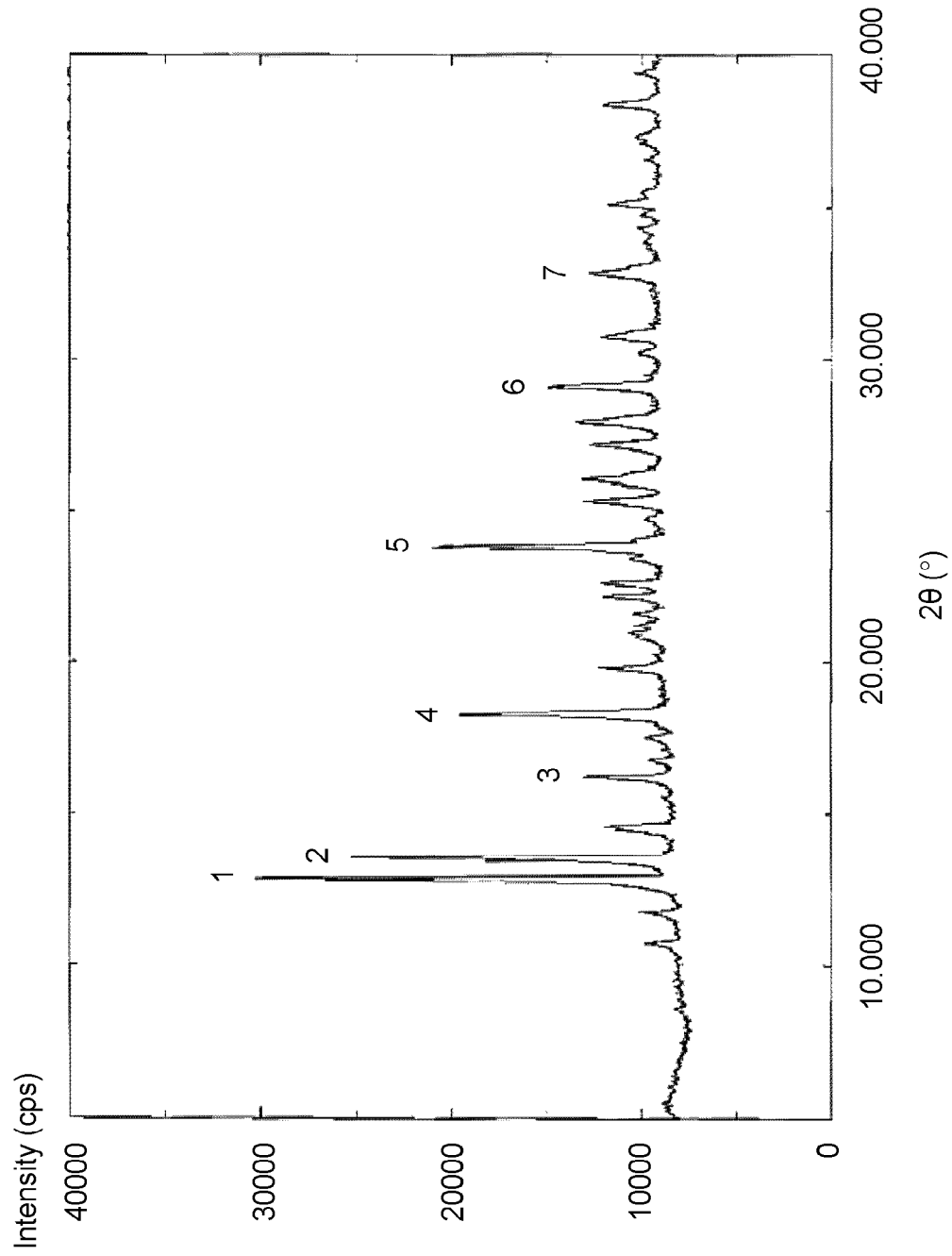
FIG. 1 illustrates a powder X-ray diffraction spectrum of the hydrochloride salt of Compound 1 (the ordinate represents intensity (cps) and the abscissa represents diffraction angle (2θ)). Characteristic peaks at 12.83°, 13.54°, 16.20°, 18.27°, 23.80°, 29.10°, and 32.83° are indicated with the numbers 1 to 7.

The compound that forms a hydrochloride salt in the present invention is 1-(2,3-dichlorobenzoyl)-4-((5-fluoro-6-(5-methyl-1H-pyrazol-3-ylamino)pyridin-2-yl)methyl)piperidine-4-carboxylic acid (Compound 1). The structure thereof is shown below.

Compound 1 is one of substituted piperidine compounds known to have the Aurora A inhibiting activity and exhibit excellent anti-tumor activity.

[Formula 1]

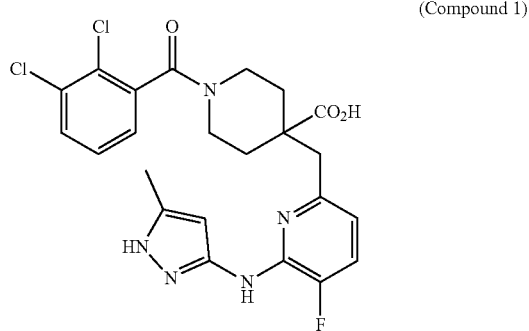

(Compound 1)

Compound 1 can be produced, for example, by the method described in Patent Literature 1. Specifically, in Patent Literature 1, Compound 1 is obtained as a white solid by purification by silica gel column chromatography and subsequent treatment with a mixture of ethanol-ethyl acetate.

As described above, Compound 1 obtained as a white solid has low solubility and formulations for oral administration prepared therefrom have been expected to have difficulty in transporting a drug into blood, since the compound in a solid state in the intestinal tract cannot pass through the intestinal membrane. Even in consideration of preparation of formulations for intravenous administration, there have been concerns that the volume of the infusion or the like becomes very large. Moreover, it was found that Compound 1 has a problem of low absorption upon oral administration.

Crystals refer to a solid in which atoms and molecules are arranged in a regular repetitive structure, and crystals are different from amorphous (non-crystalline) solids which have no repetitive structure. Crystals or amorphous solids can be examined by methods such as powder X-ray diffraction measurement (XRD measurement), differential scanning calorimetry (DSC measurement), simultaneous thermogravimetric and differential thermal analysis (TG-DTA), and infrared spectrophotometry (IR).

Crystal polymorphs refer to crystals of the same molecule in which the arrangement of atoms and molecules is different, and it is known that peaks obtained by the XRD measurement are different between crystal polymorphs.

Moreover, crystal polymorphs are known to be different in solubility, oral absorption, stability, and the like, and it is desired in the development of pharmaceutical preparations from various viewpoints to find an optimal crystal.

The present inventor has repeated diligent investigations and, as a result, found that Compound 1 forms a good salt with hydrochloric acid and this is a salt excellent in solubility and oral absorption. Furthermore, the present inventor has found that crystals of the hydrochloride salt of Compound 1 are crystals excellent in solubility, stability, oral absorption and the production process that allows the production in large quantities.

A detailed description is provided below.

As described above, Compound 1 herein is 1-(2,3-dichlorobenzoyl)-4-((5-fluoro-6-(5-methyl-1H-pyrazol-3-ylamino)pyridin-2-yl)methyl)piperidine-4-carboxylic acid, which refers to the free form, not forming salt.

The free form of Compound 1 itself may be present as crystals. Crystals of the free form of Compound 1 are obtained by the method shown in Comparative Example 4 below.

Compound 1 forms salts with acids. Generally, examples of pharmaceutically acceptable acid salts include salts with many acids such as inorganic acids such as hydrochloric acid, hydrobromic acid, hydroiodic acid, sulfuric acid, nitric acid, and phosphoric acid; and organic acids such as formic acid, acetic acid, propionic acid, oxalic acid, malonic acid, succinic acid, ascorbic acid, isoascorbic acid, mandelic acid, fumaric acid, aspartic acid, maleic acid, lactic acid, malic acid, hippuric acid, glutaric acid, adipic acid, citric acid, tartaric acid, carbonic acid, picric acid, methanesulfonic acid (mesylate), p-toluenesulfonic acid (p-tosic acid), and glutamic acid.

Moreover, Compound 1 forms salts with alkaline metals, alkaline earth metals, and other bases. Generally, examples of pharmaceutically acceptable basic salts include many salts such as potassium salts, sodium salts, calcium salts, ammonium salts, methyl ammonium salts, and dimethyl ammonium salts.

The solubility of the mesylate salt of Compound 1 is superior to that of the free form of Compound 1, but not satisfactory in comparison with that of other salts.

The absorption of the potassium salt and sodium salt of Compound 1 is superior to that of the free form of Compound 1, but these salts may change in crystal form upon temperature increase and have very high hygroscopicity and therefore not satisfactory in quality control and not suitable for the production in large quantities.

In contrast, the hydrochloride salt of Compound 1 according to the present invention (which may, hereinafter, be referred to as merely "the hydrochloride salt of the present invention") is excellent in solubility and oral absorption and crystals of the hydrochloride salt are excellent in solubility, stability, and oral absorption and can be produced in large quantities and therefore suitable as a salt for the development of pharmaceutical preparations.

The hydrochloride salt of the present invention is a salt in which the molar ratio of hydrochloric acid and Compound 1 may be 1:1, which can be determined by an analysis method such as elementary analysis, ion chromatography, or capillary electrophoresis.

The hydrochloride salt of the present invention may be a single crystal, a mixture of 2 or more crystalline polymorphs, an amorphous salt, or a mixture thereof, but is preferably a hydrochloride salt having crystals at a weight ratio of 50% or more and more preferably a hydrochloride salt having crystals at a weight ratio of 60% or more, 70% or more, 80% or more, or particularly 90% or more. The "weight ratio" herein refers to a weight percentage of particular crystals in the hydrochloride salt of the present invention.

The crystals of the hydrochloride salt of the present invention also include crystal habits different in external forms due to the difference in growth of the crystal faces. Therefore, crystals having the same pattern of peaks, but different relative intensities of peaks at the diffraction angle 2θ obtained by the XRD measurement are also included. The relative intensities herein are relative values of peak areas of peaks at the diffraction angle 2θ in powder X-ray diffraction spectrum, relative to the maximum peak area defined as 100.

In addition, the error of each peak at a diffraction angle 2θ in powder X-ray diffraction spectrum in the present invention is about ±0.2°. This is an error caused by the apparatus used in the measurement, the methods of sample preparation and data analysis, and the like. Thus, ±0.2° error of the diffraction angle 2θ obtained is taken into consideration in the XRD measurement of crystals in the present invention.

The crystals of the hydrochloride salt of the present invention have characteristic peaks at at least 3 or more diffraction angles (2θ±0.2°) selected from 12.83°, 13.54°, 16.20°, 18.27°, 23.80°, 29.10°, and 32.83° in powder X-ray diffraction spectrum. In a preferred embodiment, the crystals of the hydrochloride salt of the present invention have characteristic peaks at at least 5 or more diffraction angles (2θ±0.2°) selected from 12.83°, 13.54°, 16.20°, 18.27°, 23.80°, 29.10°, and 32.83° in powder X-ray diffraction spectrum. In a more preferred embodiment, the crystals of the hydrochloride salt of the present invention are crystals having characteristic peaks at diffraction angles (2θ±0.2°) of 12.83°, 13.54°, 16.20°, 18.27°, 23.80°, 29.10°, and 32.83° in powder X-ray diffraction spectrum. In a particularly preferred embodiment, the crystals of the hydrochloride salt of the present invention are crystals whose powder X-ray diffraction spectrum is described in FIG. 1.

As shown in Examples, the characteristic peaks at the 3 or more diffraction angles (2θ±0.2°) described above were not observed at all with the free form of Compound 1 and other salts of Compound 1.

The temperature measurement of endothermic peaks measured in DSC curves of the differential scanning calorimetry (DSC) measurement (also referred to as differential thermal analysis) produces errors due to the rate of temperature increase, the purity of samples, and the like. Thus, ±5.0° C. error of the endothermic peak (peak top value) is taken into consideration in the DSC measurement of crystals of the present invention. The term "around" used in this context means ±5.0° C.

In a typical embodiment, the hydrochloride salt of the present invention has an endothermic peak at around 234° C. (234±5° C., that is to say, 229 to 239° C.) in the DSC curve, as seen in the result of simultaneous thermogravimetric and differential thermal analysis shown in FIG. 2. As described above, the endothermic peak herein means a value at the top of the peak. Furthermore, whereas the potassium salt and sodium salt of Compound 1 have been found to be unstable with temperature increase, in the DSC curve of the hydrochloride salt of the present invention, peaks are not observed other than the peak in the vicinity of the melting point and the hydrochloride salt of the present invention is stable even under high temperatures.

The crystals of the hydrochloride salt of the present invention preferably have characteristic peaks at at least 3 or more diffraction angles (2θ±0.2°) selected from 12.83°, 13.54°, 16.20°, 18.27°, 23.80°, 29.10°, and 32.83° in powder X-ray diffraction spectrum and have an endothermic peak (peak top value) at 234±5° C. in DSC curve. More preferably, the crystals of the hydrochloride salt of the present invention have characteristic peaks at at least 5 or more diffraction angles (2θ±0.2°) selected from 12.83°, 13.54°, 16.20°, 18.27°, 23.80°, 29.10°, and 32.83° in powder X-ray diffraction spectrum and have an endothermic peak (peak top value) between 229 and 239° C. in DSC curve. Further preferably, the crystals of the mesylate salt of the present invention have characteristic peaks at diffraction angles (2θ±0.2°) of 12.83°, 13.54°, 16.20°, 18.27°, 23.80°, 29.10°, and 32.83° in powder X-ray diffraction spectrum and have an endothermic peak (peak top value) between 229 and 239° C. in DSC curve.

Moreover, the hydrochloride salt of the present invention exhibits a weight change of less than 0.5% in the dynamic vapor sorption system (DVS) analysis under the environment at a humidity of 5% to 75%, and has low hygroscopicity and excellent stability during long-term storage.

Furthermore, the hydrochloride salt of the present invention is markedly improved in oral absorption in comparison with the free form. Accordingly, the use of the hydrochloride salt of the present invention is highly beneficial in formulations intended for oral administration.

The hydrochloride salt of the present invention, or crystals thereof can be obtained by adding Compound 1 and hydrochloric acid to a particular solvent and stirring the mixture to have precipitation. Accordingly, the present invention also provides a method for producing the hydrochloride salt of Compound 1, or crystals thereof, comprising:

(1) a step of adding 1-(2,3-dichlorobenzoyl)-4-((5-fluoro-6-(5-methyl-1H-pyrazol-3-ylamino)pyridin-2-yl)methyl)piperidine-4-carboxylic acid (Compound 1) and hydrochloric acid to a solvent; and (2) a step of stirring the solvent obtained in the step (1) to precipitate the hydrochloride salt of Compound 1.

The present invention also provides the hydrochloride salt of Compound 1 or crystals thereof, produced by the method of production above.

Compound 1 used in the method for producing the hydrochloride salt of the present invention, or crystals thereof may be in an amorphous form, in crystal, in another crystalline form, or in a mixed form thereof.

The amount of hydrochloric acid to be added in the method for producing the hydrochloride salt of the present invention or crystals thereof is 1 to 30 times, preferably 1 to 10 times, and more preferably 1.1 times to 5 times of that of Compound 1 in molar ratio.

Examples of solvents that can be used in the method for producing the hydrochloride salt of the present invention, or crystals thereof include, water, a $C_{1-6}$ alcohol, a $C_{1-6}$ ester, a $C_{1-6}$ ketone, a $C_{1-6}$ ether, a $C_{1-6}$ hydrocarbon, and an aprotic polar solvent, and a mixed solvent thereof can also be used.

The $C_{1-6}$ alcohol refers to an alcohol having 1 to 6 carbon atoms, examples of which include methanol, ethanol, n-propanol, and isopropanol and preferably ethanol.

The $C_{1-6}$ ester refers to an ester having 1 to 6 carbon atoms, examples of which include methyl formate, ethyl formate, methyl acetate, ethyl acetate, isopropyl acetate, and butyl acetate, and preferably ethyl acetate.

The $C_{1-6}$ ketone refers to a ketone having 1 to 6 carbon atoms, examples of which include acetone, methyl ethyl ketone, methyl isopropyl ketone, methyl isobutyl ketone, and cyclohexanone, and preferably acetone.

The $C_{1-6}$ ether refers to an ether having 1 to 6 carbon atoms, examples of which include diethyl ether, t-butyl methyl ether, tetrahydrofuran, and 1,4-dioxane.

The $C_{1-6}$ hydrocarbon refers to a hydrocarbon having 1 to 6 carbon atoms, examples of which include n-hexane, n-pentane, n-heptane, cyclohexane, cyclopentane, and petroleum ether.

Examples of the aprotic polar solvent include acetonitrile, N-methyl-2-pyrrolidone, N,N-dimethylformamide, N,N-dimethyl acetamide, and dimethylsulfoxide.

Examples of solvents that can be used in the method for producing the hydrochloride salt of the present invention or crystals thereof include the solvents described above or a mixed solvent thereof, and the solvent is preferably water, a $C_{1-6}$ alcohol, a $C_{1-6}$ ester, a $C_{1-6}$ ketone, or a mixed solvent thereof. The solvent is more preferably a $C_{1-6}$ alcohol, a $C_{1-6}$ ester, a $C_{1-6}$ ketone, or a mixed solvent thereof and further preferably ethanol, ethyl acetate, acetone, or a mixed solvent of ethanol-ethyl acetate. The ratio of solvents in the mixed solvent of ethanol-ethyl acetate is 0.1 to 10 volumes, preferably 0.5 to 5 volumes, and more preferably 1 to 2 volumes of ethyl acetate to 1 volume of ethanol.

The amount of the solvent that can be used in the method for producing the hydrochloride salt of the present invention or crystals thereof is 1 to 100 times (volume/weight), preferably 3 to 50 times (volume/weight), and more preferably 5 to 30 times (volume/weight) of Compound 1.

The temperature in the step of precipitating the hydrochloride salt of the present invention or crystals thereof is set depending on the solvent to be used, as appropriate, from 0° C. to the boiling point of the solvent. The temperature in the step of precipitating is not necessary to be constant and heating or cooling can be conducted in the range between 0° C. and the boiling point of the solvent.

The stirring in the step of precipitating the hydrochloride salt of the present invention or crystals thereof is conducted as appropriate with a stirrer, stirring blades, a magnetic stirrer, or the like, depending on the amount of the solvent and the size of the reaction tank. The stirring rate may be 1 to 600 rpm and preferably 10 to 300 rpm.

Too short stirring time in the precipitation of a salt or crystals generally leads to insufficient precipitation and fails to obtain the salt and crystals at a high yield. Meanwhile, too long stirring time leads to the decomposition of active ingredient(s) and a decreased yield. Therefore, the stirring time should be set appropriately. The stirring time in the step of precipitating the hydrochloride salt of the present invention may be 0.5 to 72 hours, preferably 1 to 24 hours, and more preferably 2 to 12 hours.

In the step of precipitating crystals of the hydrochloride salt of the present invention, a crystal of the hydrochloride salt of Compound 1 may be added as a seed crystal. The seed crystal to be added may be 0.1 to 10% by weight of the theoretical yield of the hydrochloride salt of Compound 1 in the crystallization and preferably 1 to 3% by weight.

The hydrochloride salt of the present invention or crystals thereof precipitated in the solvent can be isolated and/or purified, for example, by known separation and/or purification means, such as collection by filtration, washing with an organic solvent, and/or drying under reduced pressure. Examples of organic solvents that can be used in the washing include the same solvents as the aforementioned solvents that can be used in the production.

The atmospheric pressure in the drying under reduced pressure is 0.1 atmosphere (atm) or less and preferably 0.05 atmosphere or less. The temperature in the drying under reduced pressure is 0° C. to 200° C. and preferably 25° C. to 100° C.

The present invention also provides a method for producing the hydrochloride salt of Compound 1, characterized by use of a solvent comprising one or two or more selected from the group of water, a $C_{1-6}$ alcohol, a $C_{1-6}$ ester, a $C_{1-6}$ ketone, a $C_{1-6}$ ether, a $C_{1-6}$ hydrocarbon, an aprotic polar solvent, and an aqueous hydrogen halide solution. The present invention also provides the hydrochloride salt of Compound 1 or crystals thereof, produced by the method of production.

Examples of the $C_{1-6}$ alcohol, $C_{1-6}$ ester, $C_{1-6}$ ketone, $C_{1-6}$ ether, $C_{1-6}$ hydrocarbon and aprotic polar solvent include the solvents respectively described above.

Examples of the aqueous hydrogen halide solution preferably include hydrochloric acid.

In one embodiment, the aforementioned hydrochloride salt of the present invention, or crystals thereof can be produced by using one or two or more solvents selected from the group of water, a $C_{1-6}$ alcohol, a $C_{1-6}$ ester, a $C_{1-6}$ ketone, a $C_{1-6}$ ether, a $C_{1-6}$ hydrocarbon, an aprotic polar solvent, and an aqueous hydrogen halide solution.

In a more specific embodiment, the aforementioned hydrochloride salt of the present invention or crystals thereof can be produced by using one or two or more solvents selected from the group of a $C_{1-6}$ alcohol, a $C_{1-6}$ ester, a $C_{1-6}$ ketone, and an aqueous hydrogen halide solution.

In a more specific embodiment, the aforementioned hydrochloride salt of the present invention or crystals thereof can be produced by using one or two or more solvents selected from the group of ethyl acetate, ethanol, and hydrochloric acid. In a particular embodiment, the aforementioned hydrochloride salt of the present invention or crystals thereof can be produced by using a mixed solvent of ethyl acetate, ethanol, and hydrochloric acid.

The hydrochloride salt of the present invention obtained by the aforementioned method comprises crystals having characteristic peaks at at least 3 or more diffraction angles (2θ±0.2° selected from 12.83°, 13.54°, 16.20°, 18.27°, 23.80°, 29.10°, and 32.83° in powder X-ray diffraction spectrum at a weight ratio to the total weight of the hydrochloride salt of 50% or more, 60% or more, 70% or more, 80% or more, or 90% or more.

Preferably, the hydrochloride salt of the present invention comprises crystals having characteristic peaks at diffraction angles (2θ±0.2°) of 12.83°, 13.54°, 16.20°, 18.27°, 23.80°, 29.10°, and 32.83° in powder X-ray diffraction spectrum at a weight ratio to the total weight of the hydrochloride salt of 50% or more, 60% or more, 70% or more, 80% or more, or 90% or more.

The hydrochloride salt of the present invention or crystals thereof obtained by the aforementioned method may be characterized by the powder X-ray diffraction spectrum shown in FIG. 1. Moreover, the hydrochloride salt of the present invention or crystals thereof obtained by the aforementioned method may be those having an endothermic peak at 234±5° C. in differential thermal analysis.

The present invention also relates to a pharmaceutical composition comprising the hydrochloride salt of the present invention. In particular, the hydrochloride salt of the present invention is useful as an antitumor agent since Compound 1 has excellent aurora A inhibitory activity. Cancer to be targeted is not particularly limited, but examples thereof include head and neck cancer, digestive organ cancer (esophageal cancer, gastric cancer, gastrointestinal stromal tumor, duodenal cancer, hepatocarcinoma, biliary cancer (gallbladder cancer, bile duct cancer, and the like), pancreatic cancer, small intestine cancer, large intestine cancer (colorectal cancer, colon cancer, rectal cancer, and the like) and the like), lung cancer, breast cancer, ovarian cancer, uterine cancer (cervical cancer, endometrial cancer, and the like), kidney cancer, bladder cancer, prostate cancer, urothelial cancer, bone sarcoma, soft tissue sarcoma, blood cancer (B-cell lymphoma, chronic lymphocytic leukemia, peripheral T-cell lymphoma, myelodysplastic syndrome, acute myeloid leukemia, acute lymphocytic leukemia, and the like), multiple myeloma, skin cancer, and mesothelioma.

The pharmaceutical composition comprising the hydrochloride salt of the present invention contains a pharmaceutical carrier(s) as needed, and can employ various dosage forms depending on the prophylactic or therapeutic purpose. The form may be, for example, any of an oral agent, an injection, a suppository, an ointment, and a patch, and is preferably an oral agent. More specifically, the pharmaceutical composition according to the present invention is preferably a pharmaceutical composition for oral administration. These various dosage forms can each be produced by methods for formulation known by or conventional to those skilled in the art. The pharmaceutical composition for oral administration can be, for example, in a form of powder, tablets, capsules, or a syrup.

As the pharmaceutical carrier, various organic or inorganic carrier substances conventional as a formulation material are used, and such a carrier is contained as an excipient, a binder, a disintegrator, a lubricant, or a colorant in a solid formulation or as a solvent, a solubilizing agent, a suspending agent, an isotonizing agent, a buffer, a soothing agent, or the like in a liquid formulation. Moreover, a formulation additive(s) such as an antiseptic, an antioxidant, a colorant, an edulcorant, or a stabilizer can also be used, as needed.

The amount of the hydrochloride salt of the present invention to be contained in each dosage unit form described above varies depending on the symptom of the patient to which it should be applied, the dosage form thereof, or the like, but it is generally desirable that the amount is 0.05 to 1000 mg for an oral agent, 0.01 to 500 mg for an injection, and 1 to 1000 mg for a suppository per dosage unit form.

Moreover, the daily dose of the agent having the dosage form described above varies depending on the symptom, body weight, age, sex, and the like of the patient and cannot generally be determined, but may usually be 0.05 to 5000 mg and preferably 0.1 to 1000 mg per adult (50 kg body weight) per day in terms of the hydrochloride salt of the present invention, and it is preferred to be administered once a day, or about 2 to 3 times a day.

EXAMPLES

Hereinafter, the present invention will be described in further detail with reference to Examples, but the present invention is not in any manner limited by these Examples. The present invention is sufficiently described by Examples, but it will be understood by those skilled in the art that various changes and modifications will be possible. Accordingly, such changes and modifications are encompassed by the present invention unless these deviate from the scope of the present invention.

The various reagents used in Examples were commercial products unless otherwise stated.

<Proton Nuclear Magnetic Resonance ($^1$H-NMR) Measurement>

The $^1$H-NMR measurement was conducted by using AL400 (400 MHz, JEOL Ltd.), a Model Mercury 400 spectrometer (400 MHz, Agilent Technologies, Inc.), or a Model Inova 400 spectrometer (400 MHz, Agilent Technologies, Inc.) equipped with a 400 M NMR probe (Protasis), and using tetramethyl silane as an internal standard when the deuterated solvent contains tetramethyl silane, and otherwise using the NMR solvent as an internal standard. All δ values were expressed in ppm in the obtained $^1$H-NMR chart.

The meanings of abbreviations are described below.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet <Powder X-Ray Diffraction Measurement (XRD Measurement)>

For the powder X-ray diffraction, a proper amount of the test substance was gently ground with a mortar made of agate as needed, and then measurement was conducted according to the following test conditions.
Equipment: Rigaku RINT-ULTIMA+2100 (manufactured by Rigaku Corporation)
Target: Cu Kα
Scan range: 5.0 to 40.0°
Step size: 0.02°
Scan speed: 0.2°/s The handling of the equipment including data processing followed methods and procedures indicated for the equipment.

<Simultaneous Thermogravimetric and Differential Thermal Analysis (DSC Measurement)>

The DSC measurement was conducted according to the following test conditions.
Equipment: TA Instruments Q1000
Sample: about 5 mg
Rate of temperature increase: 10° C./min
Measurement temperature: Room temperature to 300° C.

The handling of the equipment including data processing followed methods and procedures indicated for the equipment.

<Liquid Chromatography (HPLC) Measurement>

The measurement by liquid chromatography was conducted according to the following test conditions.
Equipment: Agilent Technologies, Inc., 1200 Series Binary LC System
Mobile phase A: 10 mM $Na_2HPO_4$ aqueous solution (pH 6.5)
Mobile phase B: Acetonitrile
Gradient: described in Table 1
Column: Ascentis Express C18, 150 mm×4.6 mm i.d., 2.7 µm
Measurement wavelength: 210 nm The handling of the equipment including data processing followed methods and procedures indicated for the equipment.

TABLE 1

| Time (min) | Mobile phase A (%) | Mobile phase B (%) |
|---|---|---|
| 0 | 95 | 5 |
| 7 | 10 | 90 |
| 9 | 10 | 90 |
| 9.1 | 95 | 5 |
| 11 | 95 | 5 |

<Dynamic Vapor Sorption System (DVS) Analysis>

The dynamic vapor sorption system (DVS) analysis was conducted under the following conditions.
Equipment: TA Instruments VTI SGA-100
Sample: about 10 mg
Measurement temperature: 25° C.
RH steps: 5-95-1% RH by 5% RH Example 1

Hydrochloride Salt of Compound 1 (No Seed Crystal)>

Compound 1 (250 mg) obtained by the method described in Patent Literature 1 was suspended in ethanol (2.0 mL) and a 4 M hydrochloric acid-ethyl acetate solution (0.18 mL) and ethyl acetate (2.8 mL) were sequentially added. The mixture was stirred at 85° C. for 6 hours. The obtained suspension was cooled to room temperature, and then a solid was collected by filtration and washed with ethyl acetate. The obtained solid was dried under reduced pressure at 100° C. to obtain the hydrochloride salt of Compound 1 (190 mg) as crystals.

A powder X-ray diffraction spectrum of the obtained crystals of the hydrochloride salt of Compound 1 is shown in FIG. 1. More specifically, characteristic peaks at diffraction angles (2θ) of 12.83°, 13.54°, 16.20°, 18.27°, 23.80°, 29.10°, and 32.83° were observed. The values of 2θ and numerical values of relative intensities (round numbers) of these peaks in FIG. 1 are as shown in the following table.

TABLE 2

| No. | 2θ (°) | Relative intensity |
|---|---|---|
| 1 | 12.83 | 100 |
| 2 | 13.54 | 84 |
| 3 | 16.20 | 43 |
| 4 | 18.27 | 64 |
| 5 | 23.80 | 70 |
| 6 | 29.10 | 49 |
| 7 | 32.83 | 43 |

Figure 2:
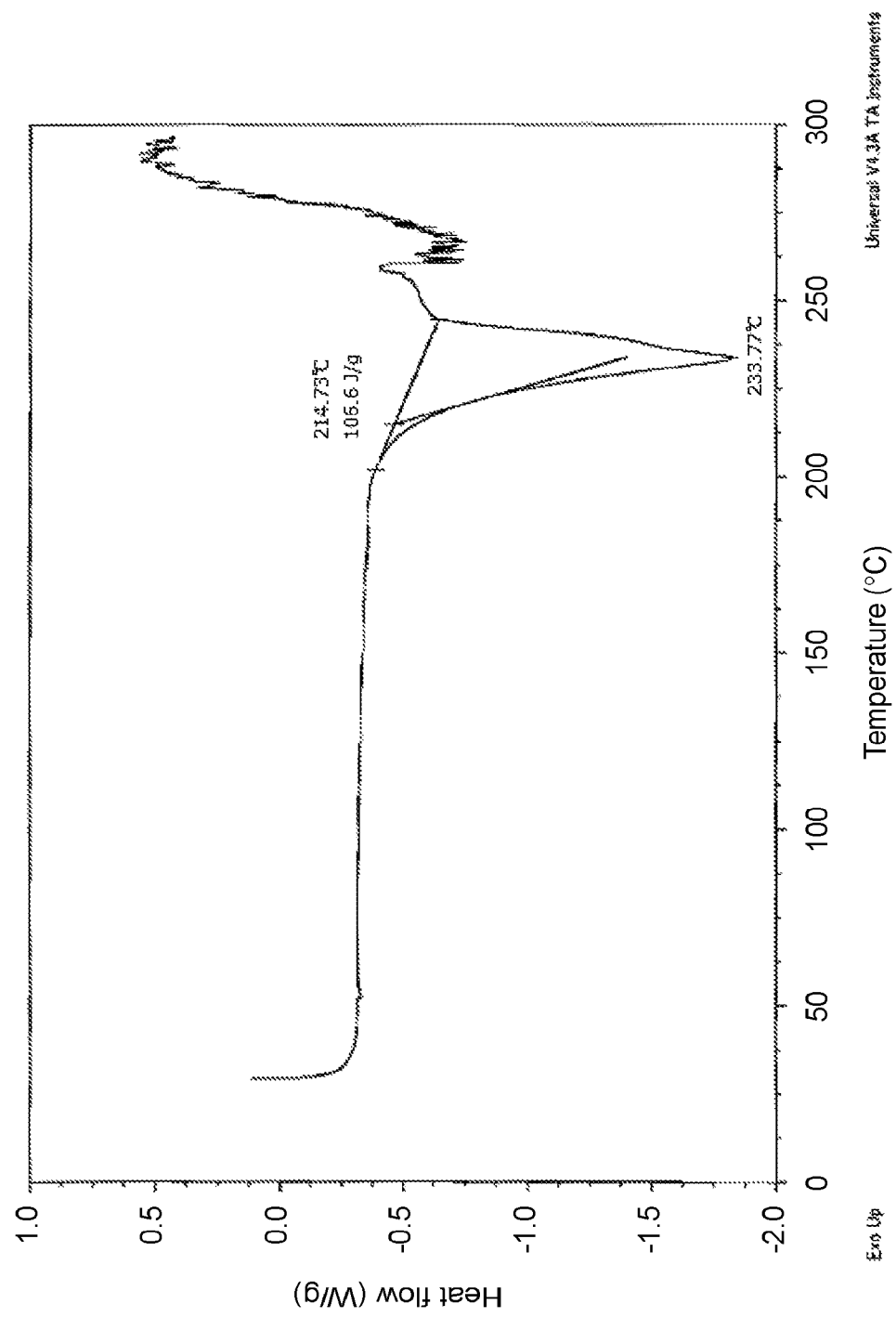
FIG. 2 illustrates a differential scanning calorimetry (DSC) curve of the hydrochloride salt of Compound 1 (the ordinate represents heat flux (W/g) and the abscissa represents temperature (° C.)).

A DSC curve in the DSC measurement of the crystals of hydrochloride salt of Compound 1 is shown in FIG. 2. The DSC curve had an endothermic peak at about 234° C. (the peak top value).

A $^1$H-NMR spectrum of the obtained compound was as follows.
$^1$H-NMR (400 MHz, DMSO-d$_6$): δppm 10.34 (2/2H, brs), 7.70-7.59 (4/2H, m), 7.46-7.37 (3/2H, m), 7.32-7.29 (1/2H, m), 6.78-6.73 (2/2H, m), 6.32 (1/2H, s), 6.30 (1/2H, s), 4.24-4.20 (2/2H, m), 3.25-3.21 (2/2H, m), 3.09-2.97 (8/2H, m), 2.31 (3/2H, s), 2.29 (3/2H, s), 2.05-2.00 (2/2H, m), 1.91-1.81 (2/2H, m), 1.68-1.52 (4/2H, m).

In this Example, the same hydrochloride salt of Compound 1 was obtained also when acetone was used instead of ethanol.

Example 2

Hydrochloride Salt of Compound 1 (in the Presence of Seed Crystal)

Compound 1 (8.46 g) obtained by the method described in Patent Literature 1 was suspended in ethanol (34 mL) and a 4 M hydrochloric acid-ethyl acetate solution (6.1 mL) and ethyl acetate (45 mL) were sequentially added. The mixture was heated to 80° C. Subsequently, crystals (around 50 mg) of the hydrochloride salt of Compound 1 obtained in Example 1 were added, and the mixture was stirred for 6 hours. The obtained suspension was cooled to 5° C., and then a solid was collected by filtration and washed with ethyl acetate. The obtained solid was dried under reduced pressure at 100° C. to obtain the hydrochloride salt of Compound 1 (8.16 g) as a white solid.

The analytical data of the obtained hydrochloride salt of Compound 1 was the same as the data obtained in Example 1.

Comparative Example 1

Mesylate Salt of Compound 1

Compound 1 (1.00 g) obtained by the method described in Patent Literature 1 was suspended in tetrahydrofuran (10 mL), and mesylic acid (methanesulfonic acid: 0.135 mL) was added and dissolved. The mixture was stirred at room temperature overnight. The precipitated solid was collected by filtration and washed with ethyl acetate. The obtained solid was dried under reduced pressure at 85° C. to obtain amorphous methanesulfonate (1.11 g).

To the obtained amorphous (300 mg) was added ethyl acetate (10 mL), and the amorphous was suspended with heating at 80° C. for 64 hours. The suspension was cooled to room temperature, and then a solid was collected by filtration and washed with ethyl acetate. The obtained solid was dried under reduced pressure at 85° C. to obtain the mesylate salt (224 mg) of Compound 1 as crystals.

Figure 3:
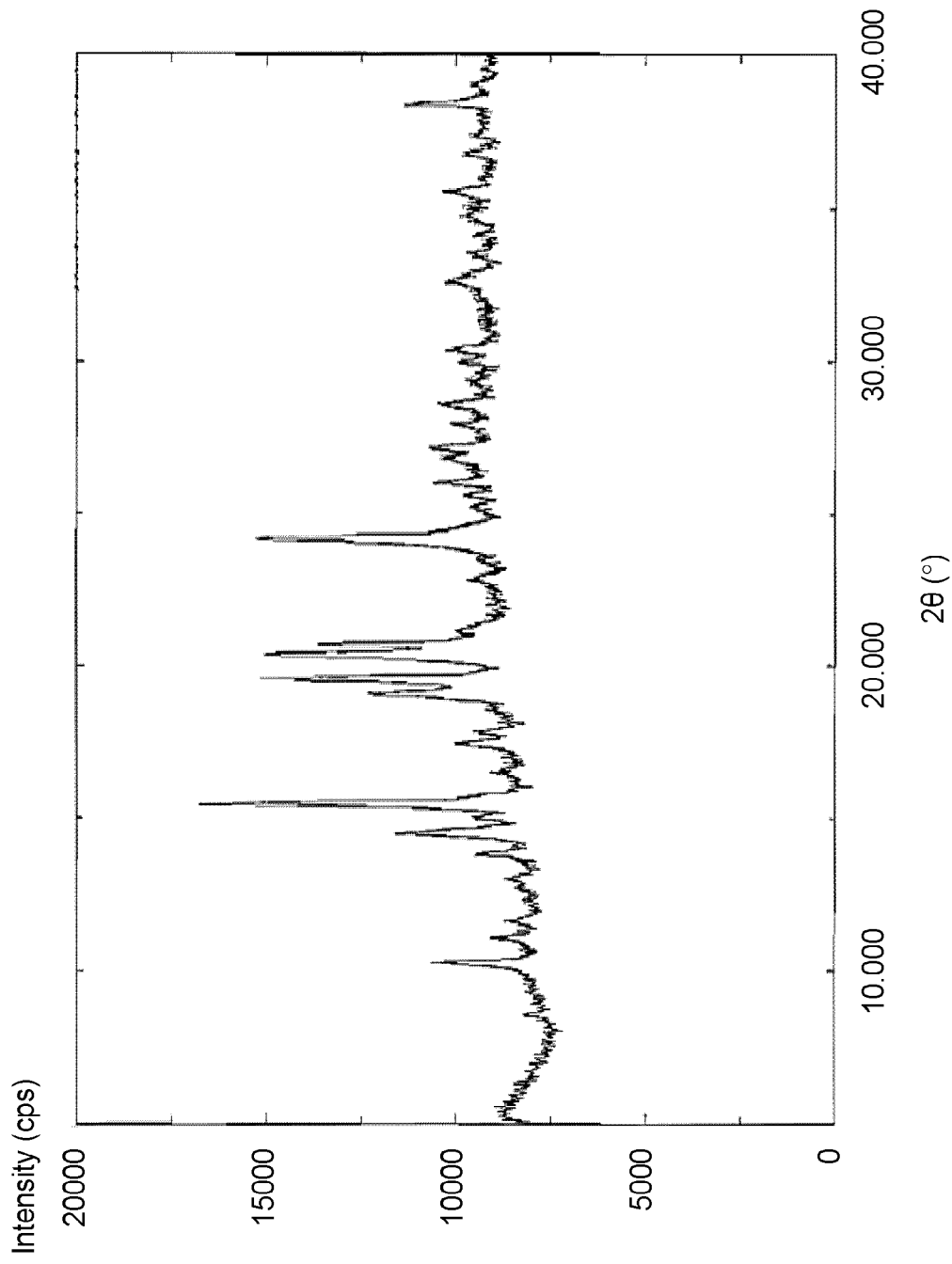
FIG. 3 illustrates a powder X-ray diffraction spectrum of the mesylate salt of Compound 1 (the ordinate represents intensity (cps) and the abscissa represents diffraction angle (2θ)).
Figure 4:
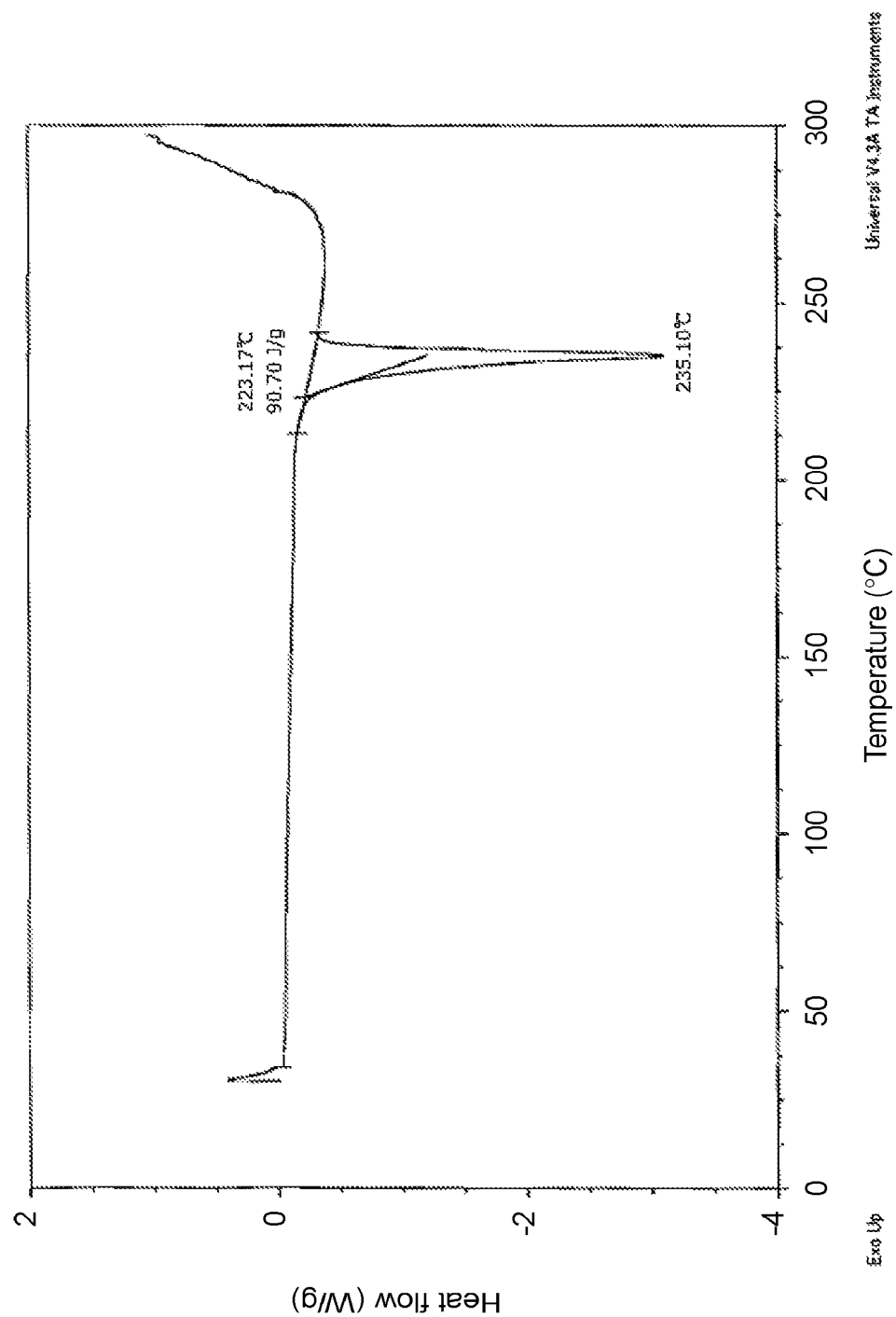
FIG. 4 illustrates a differential scanning calorimetry (DSC) curve of the mesylate salt of Compound 1 (the ordinate represents heat flux (W/g) and the abscissa represents temperature (° C.)).

A powder X-ray diffraction spectrum of the obtained crystals of the mesylate salt of Compound 1 is shown in FIG. 3. More specifically, characteristic peaks at diffraction angles (2θ) of 8.62°, 14.47°, 15.46°, 19.05°, 19.56°, 20.35°, 20.69°, 24.16°, and 26.79° were observed. A DSC curve in the DSC measurement is shown in FIG. 4.

The $^1$H-NMR spectrum of the obtained compound was as follows.
$^1$H-NMR (400 MHz, DMSO-d6): δppm 10.1 (1H, brs), 7.72-7.66 (1H, m), 7.62-7.53 (1H, m), 7.46-7.28 (2H, m), 6.75-6.67 (1H, m), 6.31-6.28 (1H, m), 4.26-4.16 (1H, m), 3.28-3.18 (1H, m), 3.12-2.94 (4H, m), 2.35-2.23 (6H, m), 2.07-2.00 (1H, m), 1.95-1.80 (1H, m), 1.68-1.48 (2H, m).

Comparative Example 2

Potassium Salt of Compound 1

To a mixture of Compound 1 (414 mg) obtained by the method described in Patent Literature 1, ethanol (20 mL), and water (5.0 mL) was added a 5 M potassium hydroxide aqueous solution (164 µL), and the mixture was heated to reflux and dissolve the compound. The mixture was cooled to room temperature and then concentrated under reduced pressure. To the obtained residue was added a mixed solvent (6 mL) of methyl ethyl ketone/water=10/1, and the mixture was heated to reflux. The obtained solution was stirred at 40°

C. for 11 hours, and the resulting suspension was stirred at room temperature overnight. A solid was collected by filtration and washed with a mixed solvent of methyl ethyl ketone/water=20/1. The obtained solid was dried under reduced pressure at 100° C. to obtain the potassium salt of Compound 1 (325 mg) as crystals.

Figure 5:
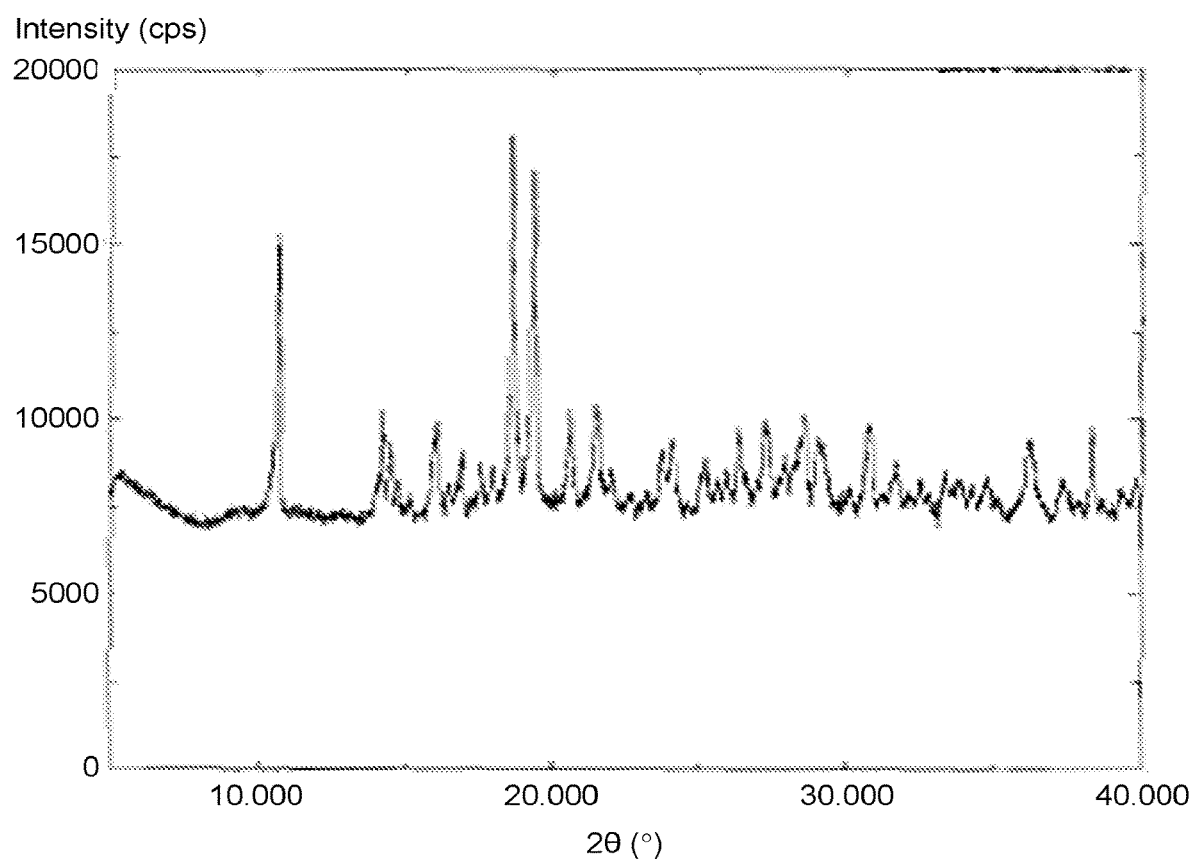
FIG. 5 illustrates a powder X-ray diffraction spectrum of the potassium salt of Compound 1 (the ordinate represents intensity (cps) and the abscissa represents diffraction angle (2θ)).
Figure 6:
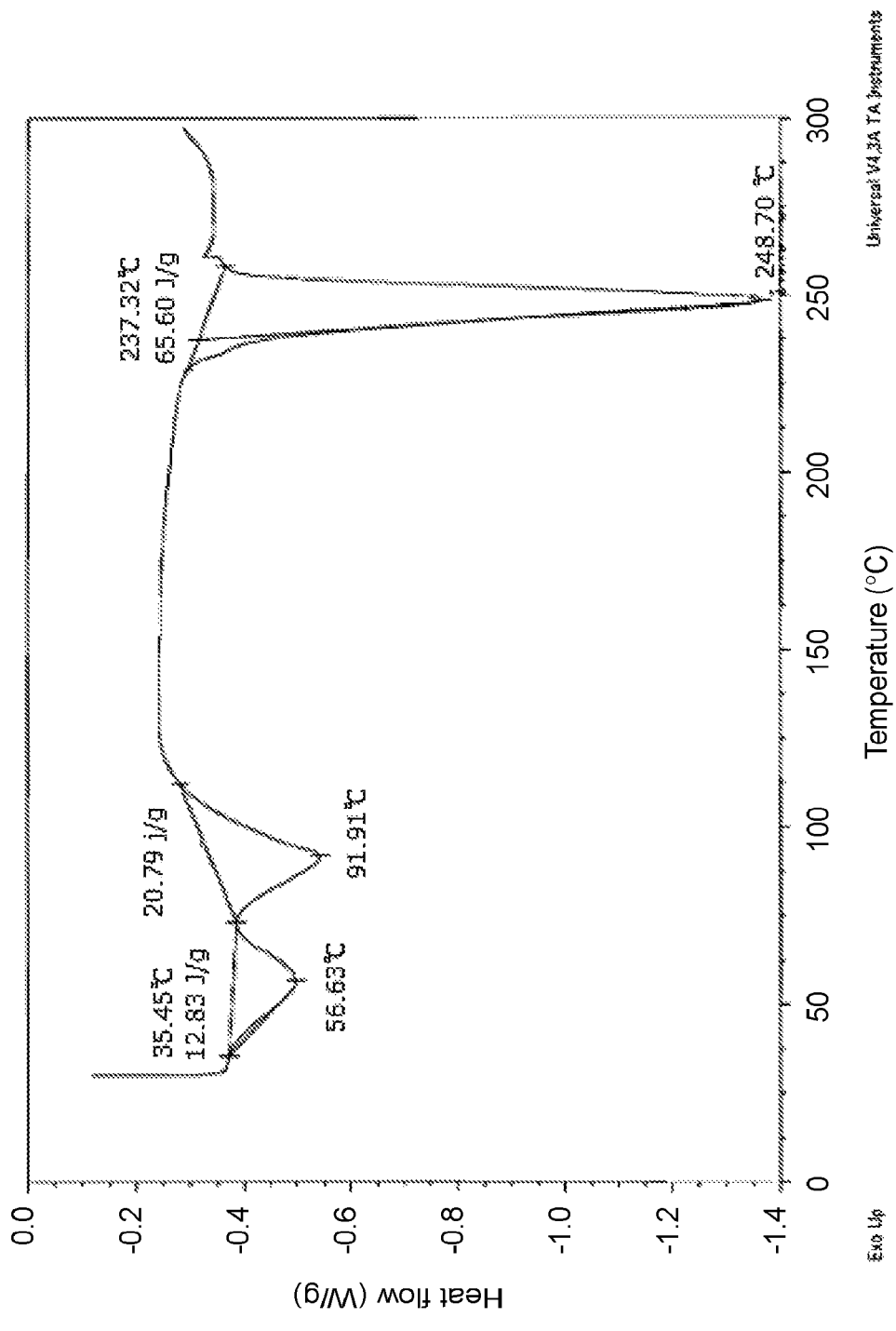
FIG. 6 illustrates a differential scanning calorimetry (DSC) curve of the potassium salt of Compound 1 (the ordinate represents heat flux (W/g) and the abscissa represents temperature (° C.)).

A powder X-ray diffraction spectrum of the obtained crystals of the potassium salt of Compound 1 is shown in FIG. 5. More specifically, characteristic peaks at diffraction angles (2θ) of 10.66°, 10.62°, 18.61°, 19.34°, 20.60°, and 21.54° were observed. A DSC curve in the DSC measurement is shown in FIG. 6.

The $^1$H-NMR spectrum of the obtained compound was as follows.

$^1$H-NMR (400 MHz, DMSO-d6): δppm 9.13 (1H, brs), 7.66-7.62 (1H, m), 7.41-7.37 (1H, m), 7.31-7.24 (2H, m), 6.52-6.51 (1H, m), 5.96 (1H, brs), 4.17-4.14 (1H, m), 3.25-3.15 (1H, m), 3.11-2.99 (2H, m), 2.78-2.63 (2H, m), 2.13-2.11 (3H, m), 2.02-1.98 (1H, m), 1.82-1.79 (1H, m), 1.29-1.15 (2H, m).

Comparative Example 3

Sodium Salt of Compound 1

To Compound 1 (250 mg) obtained by the method described in Patent Literature 1 were added a 2 M aqueous solution of sodium hydroxide (0.25 mL) and methyl ethyl ketone (10 mL), and the mixture was stirred at 70° C. for 14 hours. The mixture was cooled to room temperature, and then a solid was filtered, washed with methyl ethyl ketone, and then dried under reduced pressure to obtain the sodium salt (207 mg) of Compound 1 as colorless crystals.

Figure 7:
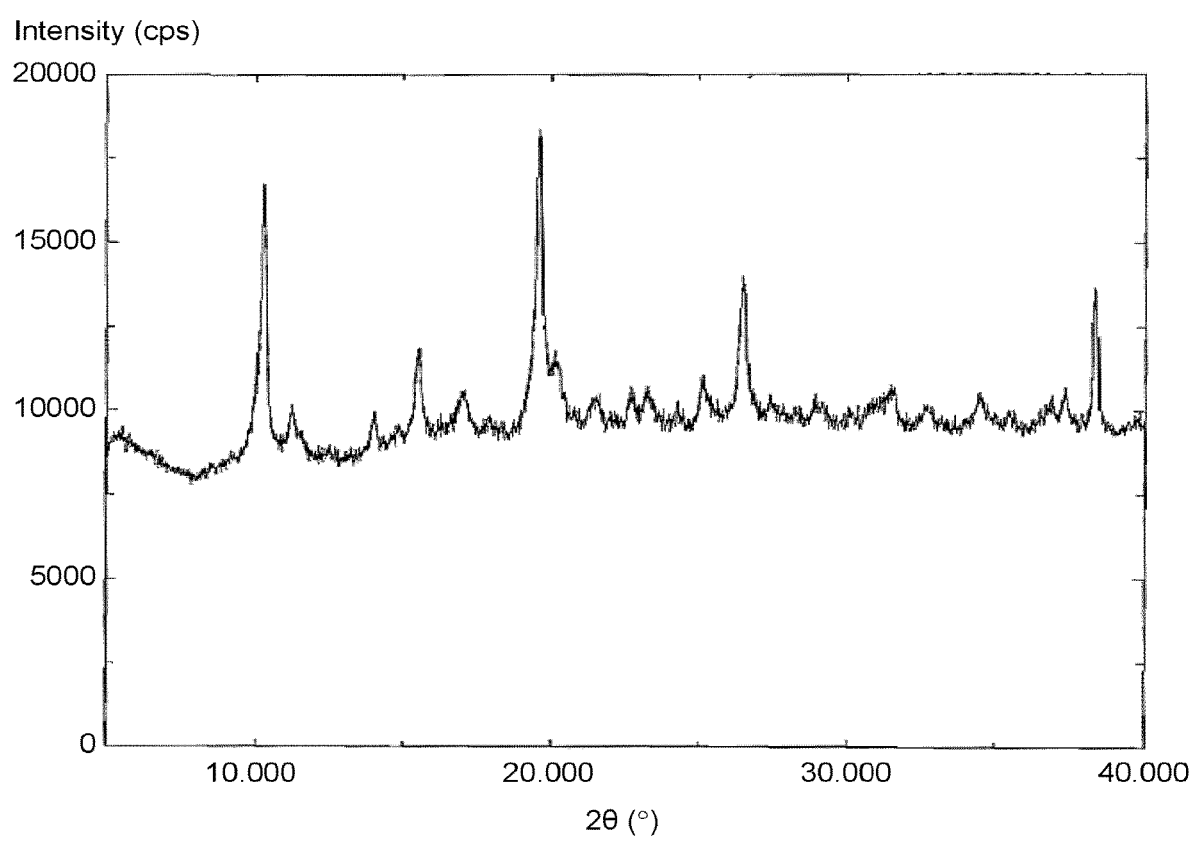
FIG. 7 illustrates a powder X-ray diffraction spectrum of the sodium salt of Compound 1 (the ordinate represents intensity (cps) and the abscissa represents diffraction angle (2θ)).
Figure 8:
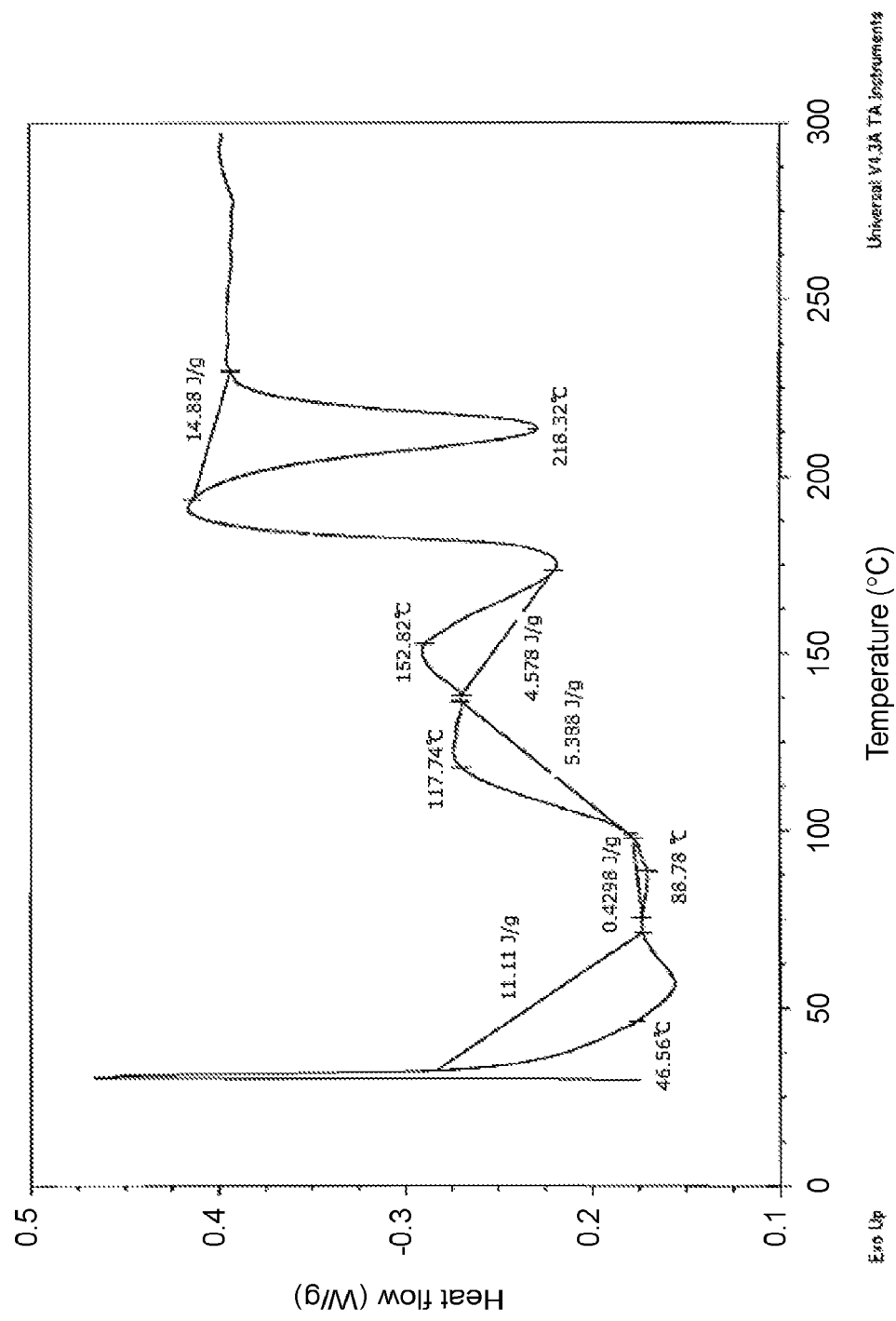
FIG. 8 illustrates a differential scanning calorimetry (DSC) curve of the sodium salt of Compound 1 (the ordinate represents heat flux (W/g) and the abscissa represents temperature (° C.)).

A powder X-ray diffraction spectrum of the obtained crystals of the sodium salt of Compound 1 is shown in FIG. 7. More specifically, characteristic peaks at diffraction angles (2θ) of 10.28°, 11.19°, 15.52°, 19.55°, and 26.48° were observed. A DSC curve in the DSC measurement is shown in FIG. 8.

The $^1$H-NMR spectrum of the obtained compound was as follows.

$^1$H-NMR (400 MHz, DMSO-d6): δppm 7.65 (1H, dd, J=6.5, 8.3 Hz), 7.47-7.18 (3H, m), 6.65-6.47 (1H, m), 4.28-4.07 (1H, d, J=9.0 Hz), 3.30-2.94 (4H, m), 2.91-2.59 (2H, m), 2.12 (3H, s), 2.05-1.69 (2H, m), 1.39-1.04 (2H, m).

Comparative Example 4

Crystal of Compound 1 (Free Form)

A mixture of Compound 1 (3.04 g) obtained by the method described in Patent Literature 1, acetic acid (6.0 mL), and 5 M hydrochloric acid (6.0 mL) was stirred at 100° C. for 1 hour to dissolve the compound, and then 25 mL of water and 6.1 mL of a 5 M sodium hydroxide aqueous solution were added at room temperature. The obtained suspension was stirred at 100° C., and ethanol (35 mL) was added. The mixture was stirred for 30 minutes. The suspension was cooled to room temperature, and then a solid was collected by filtration and washed with water and ethanol. The obtained solid was dried under reduced pressure at 50° C. to obtain a free form of Compound 1 (2.83 g) as a white solid.

Figure 9:
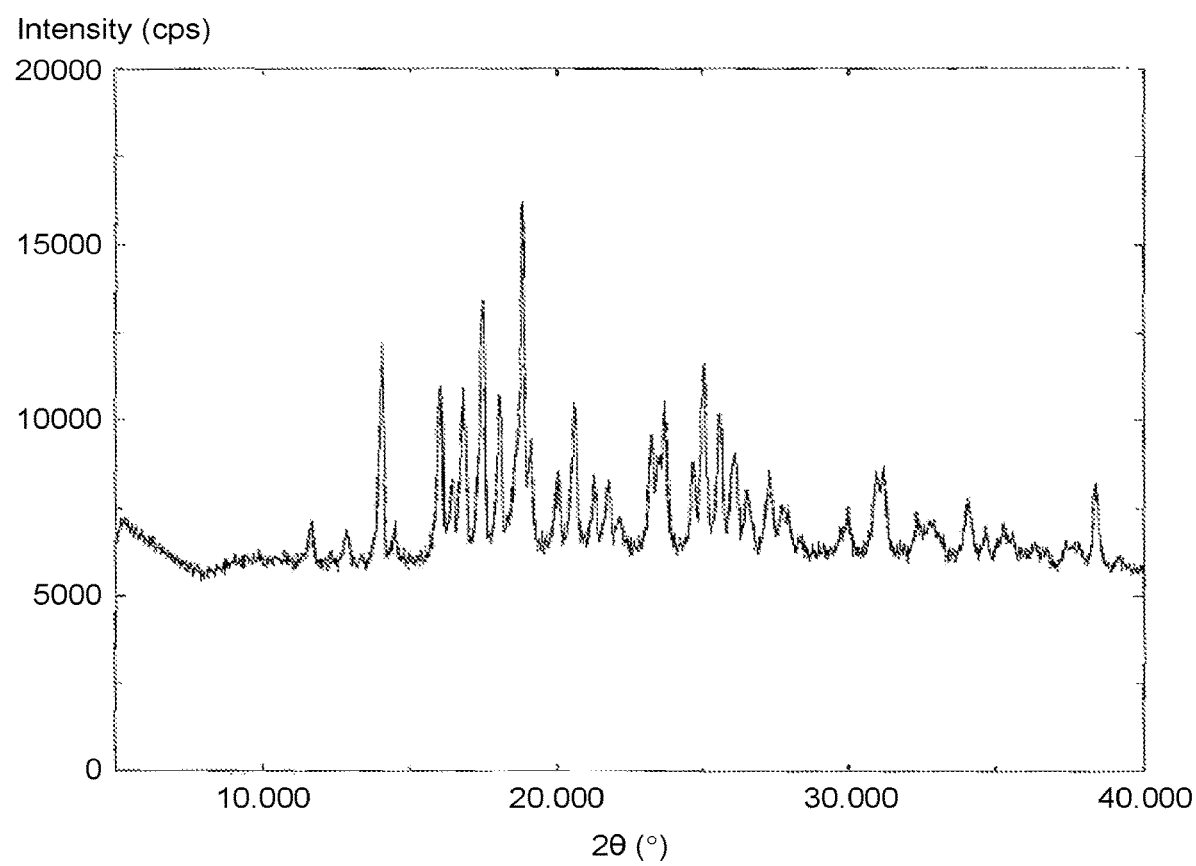
FIG. 9 illustrates a powder X-ray diffraction spectrum of the free form of Compound 1 (the ordinate represents intensity (cps) and the abscissa represents diffraction angle (2θ)).
Figure 10:
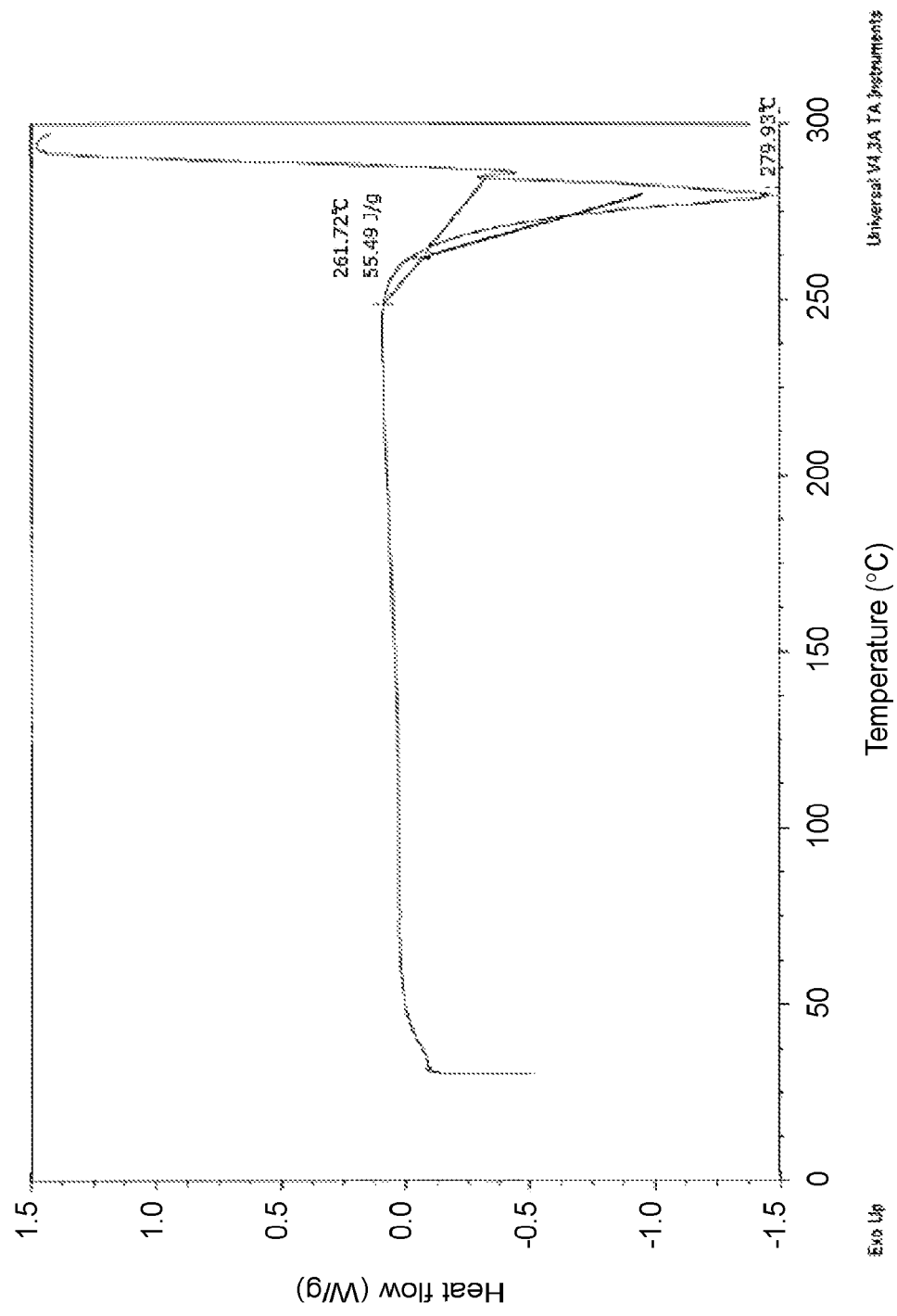
FIG. 10 illustrates a differential scanning calorimetry (DSC) curve of the free form of Compound 1 (the ordinate represents heat flux (W/g) and the abscissa represents temperature (° C.)).

A powder X-ray diffraction spectrum of the obtained crystal I of Compound 1 is shown in FIG. 9. More specifically, characteristic peaks at diffraction angles (2θ) of 12.97°, 14.10°, 16.14°, 16.81°, 17.56°, 18.90°, 19.19°, 20.68°, 24.79°, 25.07°, and 30.98° were observed. A DSC curve in the DSC measurement is shown in FIG. 10.

Test Example 1-1

Stability Test (Purity)

The crystals of the hydrochloride salt, the mesylate salt, the potassium salt, the sodium salt, and the free form of Compound 1 obtained in Example 1 and Comparative Examples 1 to 4 were each left under conditions at 40° C. (open system), at 60° C. (open system), and under light irradiation (1200000 Lux·hr) for 1 month. Subsequent measurement of purity by liquid chromatography indicated the purity change between before and after the test was 0.2% or less in any of the conditions. The results of the hydrochloride salt and the potassium salt are shown in Table 3.

TABLE 3

| Test substance | Before starting test | 40° C. (open system) | 60° C. (open system) | Under light irradiation |
|---|---|---|---|---|
| Hydrochloride salt | 99.4 | 99.2 | 99.3 | 99.4 |
| Potassium salt | 99.8 | 99.7 | 99.8 | 99.8 |

Values in the table indicate the purity (%) in samples.

From the foregoing results, the crystals of the hydrochloride salt, the mesylate salt, the potassium salt, the sodium salt, and the free form of Compound 1 were all found to be crystals excellent in stability as solid.

Test Example 1-2

Stability Test (Solid Change)>

As a result of the DSC measurement of the crystals of the hydrochloride salts of Compound 1 of Example 1 and the mesylate salt, the potassium salt, the sodium salt, and the free form of Comparative Examples 1 to 4, charts suggesting endothermic and exothermic processes at relatively low temperatures were obtained for the potassium salt and the sodium salt (FIGS. 6 and 8), but such charts were not obtained for the hydrochloride salt, the mesylate salt, and the free form (FIGS. 2, 4, and 10).

From the foregoing results, the crystals of the potassium salt and the sodium salt of Compound 1 were found to be crystals at high risk of changing the crystal form with temperature increase.

Test Example 2

Solubility Measurement

The solubility measurement was conducted on the hydrochloride salt, the mesylate salt, the potassium salt, and the sodium salt of Compound 1 and the free form of Compound 1. Specifically, the solubility of the samples: the crystals of the hydrochloride salt of Compound 1 produced in Example 1; the crystals of the mesylate salt of Compound 1 produced in Comparative Example 1; the crystals of the potassium salt of Compound 1 produced in Comparative Example 2; the crystals of the sodium salt of Compound 1 produced in Comparative Example 3; and the crystal of the free form of Compound 1, in the 1st and 2nd fluids for dissolution test according to Japanese Pharmacopoeia was measured according to Japanese Pharmacopoeia, Dissolution test. The results are shown in Table 4. From these results, the hydrochloride salt, the potassium salt, and the sodium salt of Compound 1 were found to be superior in solubility to the mesylate salt and the free form.

TABLE 4

| Test substance | 1st fluid for dissolution test μg/mL | 2nd fluid for dissolution test μg/mL |
|---|---|---|
| Hydrochloride salt | >1000 | >1000 |
| Mesylate salt | 490 | 420 |
| Potassium salt | >1000 | 730 |
| Sodium salt | >1000 | >1000 |
| Free form | 24 | 6 |

Test Example 3

Dynamic Vapor Sorption System (DVS) Analysis

The hygroscopicity of the hydrochloride salt of Compound 1 obtained in Example 1 and the potassium salt obtained in Comparative Example 2 was examined by dynamic vapor sorption system (DVS) analysis. The adsorption and desorption data was collected at 5% relative humidity (RH) intervals in the range of 5% to 95% RH. Before the measurement, the temperature was increased at 1° C./min to 25° C. under nitrogen purging and the salts were dried for up to 6 hours until the weight change in 5 minutes became less than 0.0100%. At the time of the measurement, up to 2 hours of equilibration was conducted until the weight change in 5 minutes became less than 0.0100%.

Figure 11:
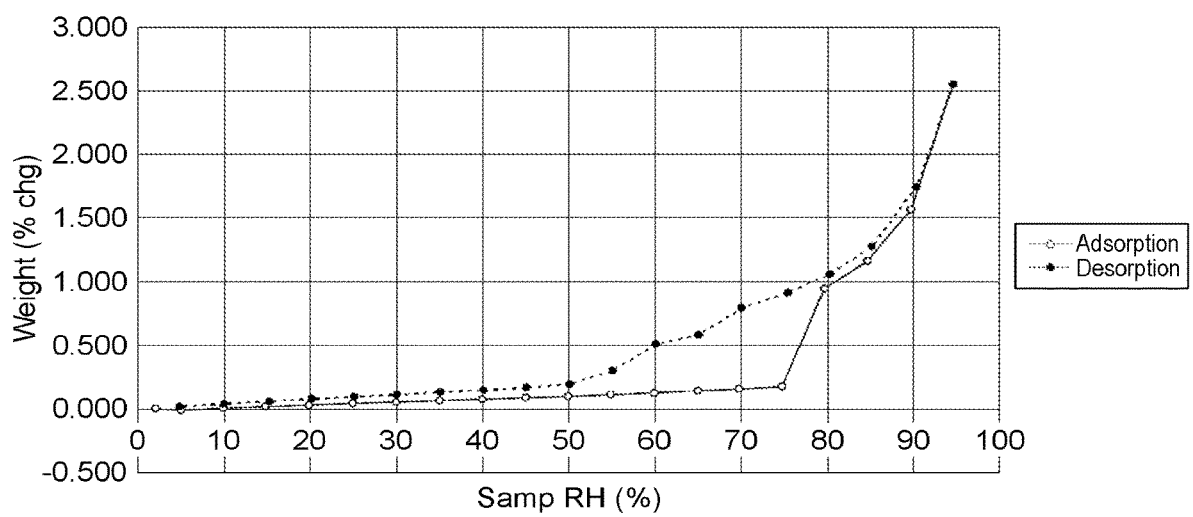
FIG. 11 illustrates a result of dynamic vapor sorption system (DVS) analysis (water vapor sorption/desorption test) of the hydrochloride salt of Compound 1 (the ordinate represents weight (% chg) and the abscissa represents relative humidity (%) in the sample environment).
Figure 12:
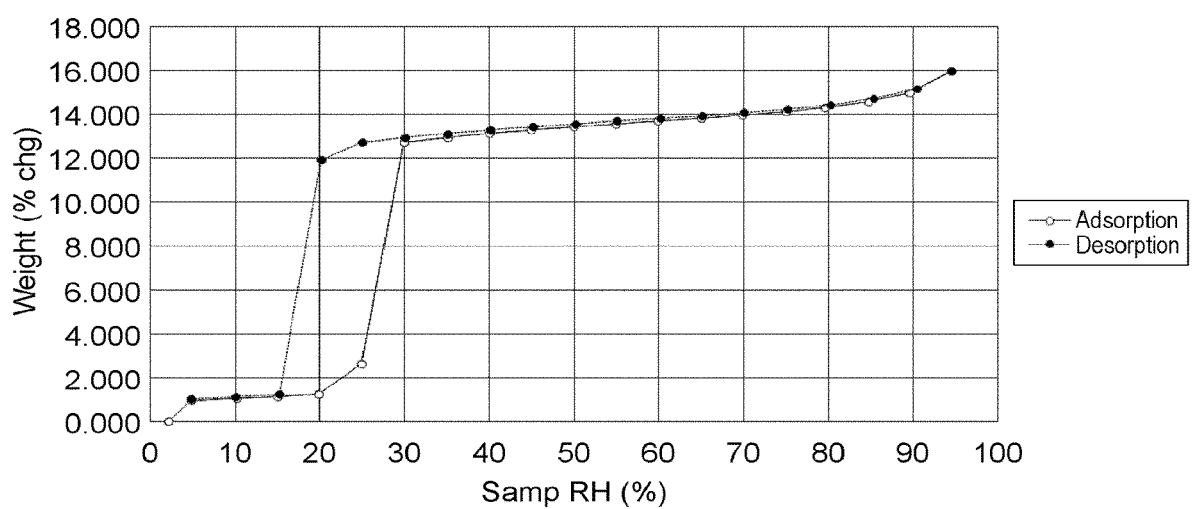
FIG. 12 illustrates a result of dynamic vapor sorption system (DVS) analysis (water vapor sorption/desorption test) of the potassium salt of Compound 1 (the ordinate represents weight (% chg) and the abscissa represents relative humidity (%) in the sample environment).

The result of the hydrochloride salt of Compound 1 is shown in FIG. 11 and the result of the potassium salt is shown in FIG. 12. From these results, it was confirmed that the weight change of the hydrochloride salt of Compound 1 during the increase of humidity from 5% to 75% was less than 0.5%, while the weight change of the potassium salt exceeded 14%. Similarly, a weight change of 40% or more was confirmed in the sodium salt of Compound 1 (data not shown). Therefore, it was found that the hydrochloride salt of Compound 1 is a salt that is very slightly affected by the ambient humidity and that the potassium salt and the sodium salt are salts susceptible to the ambient humidity. Being susceptible to the humidity may decrease the stability and also makes quality control difficult. Therefore, the potassium salt and the sodium salt were found to be not suitable for the production in large quantities.

Test Example 4

Absorption Test

The hydrochloride salt of Compound 1 was suspended in 0.5% HPMC, and orally administered to BALB/cA mice at 50 mg/kg in terms of the dose of Compound 1. At 0.5, 1, 2, 4, and 6 hours after the oral administration, the blood was collected from the eyeground, and the plasma was obtained. The compound concentration in the obtained plasma was measured by LC/MS (Agilent Technologies Inc. Agilent 1200, AB Sciex Pte. Ltd. AB Sciex API400) and the oral absorption was evaluated.

As a result, a sufficient plasma concentration of the hydrochloride salt of Compound 1 was observed and good oral absorption was indicated, as shown in Table 5. Meanwhile, no sufficient oral absorption of the free form of Compound 1 was indicated, and it was considered that the free form is difficult to be contained in formulations for oral administration as an active ingredient and a clinical effect cannot be expected in the oral administration.

TABLE 5

| Test substance | Plasma concentration $AUC_{0-6 h}$ μM · hr |
|---|---|
| Hydrochloride salt | 18.2 |
| Free form | 0.43 |

INDUSTRIAL APPLICABILITY

Compound 1 according to the present invention is a compound that has aurora A inhibitory activity and exhibits excellent anti-tumor activity. The hydrochloride salt thereof is excellent in solubility and oral absorption, and crystals of the salt are excellent in solubility, stability, and oral absorption and can be produced in large quantities. Therefore, the hydrochloride salt of Compound 1, or crystals of the salt is promising in use in pharmaceutical preparations, particularly pharmaceutical preparations for oral administration, and antitumor agents for oral administration among all.

All publications, patents and patent applications cited herein shall be incorporated herein by reference in their entirety.

The invention claimed is:

1. A hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid,
    wherein the salt is a crystal having characteristic peaks at at least 3 or more diffraction angles (2θ±0.2°) selected from 12.83°, 13.54°, 16.20°, 18.27°, 23.80°, 29.10°, and 32.83° in powder X-ray diffraction spectrum.

2. The salt according to claim 1, wherein the salt is a crystal having characteristic peaks at diffraction angles (2θ±0.2°) of 12.83°, 13.54°, 16.20°, 18.27°, 23.80°, 29.10°, and 32.83° in powder X-ray diffraction spectrum.

3. The salt according to claim 1, wherein the salt has an endothermic peak at 234±5° C. in differential thermal analysis.

4. The salt according to claim 1, wherein a weight ratio is 90% or more.

5. A pharmaceutical composition comprising:
    the salt according to claim 1; and
    a pharmaceutical carrier.

6. The composition according to claim 5, wherein the composition is suitable for oral administration.

7. A method for producing a hydrochloride salt of 1-(2, 3-dichlorobenzoyl)-4-((5-fluoro-6-(5-methyl-1H-pyrazol-3-ylamino)pyridin-2-yl)methyl)piperidine-4-carboxylic acid according to claim 1, the method comprising:
    adding 1-(2,3-dichlorobenzoyl)-4-((5-fluoro-6-(5-methyl-1H-pyrazol-3-ylamino)pyridin-2-yl)methyl)piperidine-4-carboxylic acid and hydrochloric acid to a solvent; and
    stirring the solvent obtained in the adding to precipitate a hydrochloride salt of 1-(2,3-dichlorobenzoyl)-4-((5-fluoro-6-(5-methyl-1H-pyrazol-3-ylamino)pyridin-2-yl)methyl)piperidine-4-carboxylic acid.

8. The method according to claim 7, wherein the solvent in the adding is selected from a $C_{1-6}$ alcohol, a $C_{1-6}$ ester, a $C_{1-6}$ ketone, or a mixed solvent thereof.

9. The method according to claim 7, wherein the solvent in adding is selected from the group consisting of water, a $C_{1-6}$ alcohol, a $C_{1-6}$ ester, a $C_{1-6}$ ketone, a $C_{1-6}$ ether, a $C_{1-6}$ hydrocarbon, an aprotic polar solvent, and an aqueous hydrogen halide solution.

\* \* \* \* \*